United States Patent [19]
Mikuni et al.

[11] Patent Number: 5,290,838
[45] Date of Patent: Mar. 1, 1994

[54] α-CYANOACRYLATE CONTAINING ADHESIVE COMPOSITION

[75] Inventors: Hiroyuki Mikuni, Sagamihara; Toshiyuki Chikusa, Hachioji, both of Japan

[73] Assignee: Three Bond Co., Ltd., Tokyo, Japan

[21] Appl. No.: 943,507

[22] Filed: Sep. 11, 1992

Related U.S. Application Data

[62] Division of Ser. No. 732,457, Jul. 18, 1991, Pat. No. 5,175,337.

[30] Foreign Application Priority Data

Aug. 7, 1990 [JP] Japan .................................. 2-207679

[51] Int. Cl.$^5$ ....................... C08K 5/42; C08F 220/10
[52] U.S. Cl. ..................................... 524/157; 524/167; 524/173; 524/284; 524/405; 524/345; 524/346; 524/347; 524/349; 524/392; 526/328.5
[58] Field of Search ................ 558/443, 457; 428/463, 428/552; 526/298, 378.5; 524/157, 167, 173, 284, 405, 345, 346, 347, 349, 392

[56] References Cited

U.S. PATENT DOCUMENTS

| | | | |
|---|---|---|---|
| 2,794,788 | 6/1957 | Coover, Jr. et al. | 558/443 X |
| 2,816,093 | 12/1957 | Coover, Jr. | 558/443 X |
| 3,142,698 | 7/1964 | Halpern et al. | 558/443 X |
| 3,465,027 | 9/1969 | Hawkins | 558/443 X |
| 3,527,841 | 9/1970 | Wicker, Jr. et al. | 558/443 X |
| 3,728,375 | 4/1973 | Coover, Jr. et al. | 558/443 |
| 4,297,160 | 10/1981 | Kusayama et al. | 428/463 X |

FOREIGN PATENT DOCUMENTS 0470722A 2/1992 European Pat. Off. ............ 558/443

*Primary Examiner*—Joseph Paul Brust
*Attorney, Agent, or Firm*—Scully, Scott, Murphy & Presser

[57] ABSTRACT

A novel neopentyl α-cyanoacrylate composition is provided. The composition which includes neopentyl α-cyanoacrylate has superior adhesive properties even at high temperatures and is characterized by the absence of the whitening phenomenon.

7 Claims, No Drawings

α-CYANOACRYLATE CONTAINING ADHESIVE COMPOSITION

This is a divisional of U.S. Pat. application Ser. No. 07/732,457, filed on Jul. 18, 1991 and now U.S. Pat. No. 5,175,337.

BACKGROUND OF THE INVENTION

The present invention relates to a novel α-cyanoacrylate and a cyanoacrylate-based adhesive composition containing same.

α-Cyanoacrylates such as methyl α-cyanoacrylate and ethyl α-cyanoacrylate are polymerized and cured rapidly by the action of a small amount of water present on the surface of a material to be bonded and afford an adhesive force of an extremely high strength, so are widely used as room-temperature one-pack type instantaneous adhesives for the bonding of metals, plastics, rubber, wood and the like.

As α-cyanoacrylate there are known propyl α-cyanoacrylate, allyl α-cyanoacrylate, propargyl α-cyanoacrylate, 2,2,2-trifluoroethyl α-cyanoacrylate, 2,2,3,3-tetrafluoropropyl α-cyanoacrylate, 2-methoxyethyl α-cyanoacrylate, 2-ethoxyethyl α-cyanoacrylate and the like in addition to the above mentioned methyl and ethyl α-cyanoacrylates.

Generally, in the case where an α-cyanoacrylate is used as an adhesive, a portion thereof voltilizes and is polymerized by water contained in the air and adheres as white powder to the surrounding portion of a bonded part (whitening phenomenon), thus impairing the appearance of the bonded material. When used in the assembly of electric and electronic parts, the volatilized monomer contaminates a contact portion and causes defective contact, or cures in a moving part, thereby causing malfunction. Moreover, the thermal stability of a cured product is not sufficient and the bonding strength is reduced rapidly over 100° C. It is known that α-cyanoacrylates having an unsaturated bond in the ester portion have improved thermal stability. In this case the cured or adhered portion is heat treated at an appropriate temperature (100° C.-150° C.) in order to improve the thermal stability. However, the adhesive properties at a high temperature are not improved.

It is the object of the present invention to overcome the above mentioned drawbacks of the prior art. More concretely, it is the object of the present invention to provide a novel compound having superior adhesive properties as an instantaneous adhesive and superior in whitening-preventing property and thermal stability including high temperature adhesive properties.

SUMMARY OF THE INVENTION

The present invention resides in a novel neopentyl α-cyanoacrylate having the chemical structural formula:

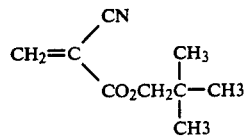

and an adhesive containing the above compound as an essential component.

DETAILED DESCRIPTION OF THE INVENTION

The novel compound, neopentyl α-cyanoacrylate exhibits excellent instantaneous adhesive properties. It has a melting point of 40° C. and is a solid at a room temperature. It can be used itself as a hot-melt type instantaneous adhesive and also used as a liquid instantaneous adhesive in admixture of conventional one or more cyanoacrylates in the same manner as conventional instantaneous adhesives. The instantaneous adhesive containing neopentyl α-cyanoacrylate as an essential component does not induce the whitening phenomenon and is superior in thermal stability, especially in high temperature-bonding strength.

Neopentyl α-cyanoacrylate may be used alone or in combination with conventional one or more α-cyanoacrylates.

Such conventional α-cyanoacrylates are those represented by the following general formula:

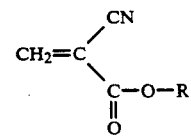

wherein R is a hydrocarbon group such as alkyl, alkenyl, or alkynyl, or an alkoxy hyrocarbon group such as alkoxyalkyl. Examples are methyl α-cyanocrylate, ethyl α-cyanoacrylate isopropyl α-cyanoacrylate, those wherein R is alkoxyalkyl, e.g. 2-methoxyethyl α-cyanoacrylate and 2-ethoxyethyl α-cyanoacrylate, those wherein R is alkenyl, e.g. allyl α-cyanoacrylate, and those wherein R is alkynyl, e.g. propargyl α-cyanoacrylate.

When using conventional cyanoacrylates in combination with neopentyl α-cyanoacrylate, the latter is preferably in an amount of 85 wt % or less, more preferably 5 to 85 wt % based on the weight of adhesive components. If the amount of neopentyl α-cyanoacrylate is more than 85 wt %, the composition becomes a solid at room temperature (i.e. 20° C.).

Neopentyl α-cyanoacrylate of the present invention may be prepared by the following reactions.

Neopentyl α-cyanoacetate having the following structural formula:

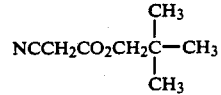

is prepared and then it is reacted with formaldehyde or paraformaldehyde in the presence of a basic catalyst to produce a condensation polymer, and then the condensation polymer thus produced is heat-depolymerized or thermally decomposed to produce neopentyl α-cyanoacrylate.

Neopentyl α-cyanoacrylate thus obtained is a solid at a room temperature but it is desirable to add thereto a stabilizer in order to store it more stably. Examples of such stabilizer include, as anionic polymerization inhibitors, sulfurous acid ($SO_2$), sulfone compounds, organic sulfonic acids, mercaptans, trifluoroacetic acid, and fluoroboric acid, and as radical polymerization inhibitors, quinones, catechol, pyrogallol, and 2,6-di-t-butylphenol. The amount of these stabilizers differs depending on the respective inhibiting abilities, but is preferably in the range of 1 to 10,000 ppm, more preferably 10 to 1,000 ppm, relative to the monomer.

The following examples are given to illustrate the present invention in more detail. The "part" and "%" in the following description are all by weight.

EXAMPLE 1

Preparation of Neopentyl α-Cyanoacetate 51 g (0.6 mole) of cyanoacetic acid, 74 g (0.84 mole) of neopentyl alcohol, 1 g of sulfuric acid and 100 g of toluene were reacted under reflux and water produced was removed by azeotropic distillation. Thereafter, the mixture thus produced was cooled to a room temperature and filtered to remove insoluble matter. The filtrate was washed with water and dried overnight with magnesium sulfate. Then, the desiccant was filtered off and the solvent was removed under a reduced pressure, followed by vacuum distillation to afford 87.1 g of neopentyl α-cyanoacrylate (b.p. 79°–81° C./3 mmHg, yield 94%).

IR (neat)cm$^{-1}$: 2262, 1751 60 MHz $^1$H-NMR (CDCl$_3$/TMS)

δ(ppm): 3.87 (s, 2H), 3.46 (s, 2H), 0.97 (s, 9H) 90 MHz $^{13}$C-NMR (CDCl$_3$)

δ(ppm): 162.91, 113.06, 75.41, 31.03, 25.86, 24.30.

Preparation of Neopentyl α-Cyanoacrylate 46.5 (0.3 mole) of neopentyl α-cyanoacetate, 8.1 g (0.27 mole) of paraformaldehyde, 140 g of toluene and 46.5 mg of triethylenediamine were reacted together under reflux and water was removed by azeotropic distillation. Then, 23.5 g of dioctyl phthalate, 0.465 g of hydroquinone and 0.93 g of phosphorus pentoxide were added and depolymerization allowed to take place at 150°–210° C. under a reduced pressure tO afford 21.65 g of crude neopentyl α-cyanoacrylate. Redistillation thereof afforded (8.3 g of neopentyl α-cyanoacrylate (b.p. 65°–67° C./2 mmHg, m.p. 40°–41° C., yield 36%).

60 MHz $^1$H-NMR (CDCl$_3$/TMS)

δ(ppm): 7.01 (s, 1H), 6.61 (s, 1H), 3.95 (s, 2H) 1.20 (s, 9H)

90MHz $^{13}$C-NMR (CDCl$_3$)

δ(ppm): 160.14, 142.78, 116.44, 114.08, 75.46, 31.22, 25.95.

EXAMPLE 2

Adhesives were prepared by mixing neopentyl α-cyanoacrylate (NPCA) and ethyl α-cyanoacrylate (ECA) as a conventional α-cyanoacrylate in such proportions as shown Table 1 below and then incorporating therein 20 ppm of BF$_3$ ethyl ether complex and 1,000 ppm of hydroquinone. Their adhesive properties are as set forth in Table 1.

TABLE 1

| Mixing Ratio (parts) NPCA/ECA | Adhesive Properties (iron/iron) | | |
|---|---|---|---|
| | Tensile Shear Strength (kgf/cm$^2$) | Hot Tensile Shear Strength (kgf/cm$^2$) | Whitening |
| 1/100 (Comparative example) | 70 | 5 | Whitened |
| 20/80 | 83 | 7 | slightly whitened |
| 40/60 | 85 | 10 | slightly whitened |
| 60/40 | 112 | 40 | not whitened |

TABLE 1-continued

| Mixing Ratio (parts) NPCA/ECA | Adhesive Properties (iron/iron) | | |
|---|---|---|---|
| | Tensile Shear Strength (kgf/cm$^2$) | Hot Tensile Shear Strength (kgf/cm$^2$) | Whitening |
| 80/20 | 124 | 45 | not whitened |
| 100/0 | 130 | 45 | not whitened |

EXAMPLE 3

Adhesives were prepared by mixing neopentyl α-cyanoacrylate (NPCA) and allyl α-cyanoacrylate (ACA) as a conventional α-cyanoacrylate in such proportions as shown in Table 2 below and then incorporating therein 20 ppm of BF$_3$ ethyl ether complex and 1,000 ppm of hydroquinone. Their adhesive properties are as set forth in Table 2.

TABLE 2

| Mixing Ratio (parts) NPCA/ECA | Adhesive Properties (iron/iron) | | |
|---|---|---|---|
| | Tensile Shear Strength (kgf/cm$^2$) | Hot Tensile Shear Strength (kgf/cm$^2$) | Whitening |
| 1/100 (Comparative example) | 100 | 5 | Whitened |
| 20/80 | 110 | 12 | slightly whitened |
| 40/60 | 113 | 23 | slightly whitened |
| 60/40 | 129 | 45 | not whitened |
| 80/20 | 130 | 45 | not whitened |
| 100/0 | 130 | 45 | not whitened |

EXAMPLE 4

Adhesives were prepared by mixing neopentyl α-cyanoacrylate (NPCA) and 2-ethoxyethyl α-cyanoacrylate (EECA) as a conventional α-cyanoacrylate in such proportions as shown in Table 3 below and then incorporating therein 20 ppm of BF$_3$ ethyl ether complex and 1,000 ppm of hydroquinone. Their adhesive properties are as set forth in Table 3.

TABLE 3

| Mixing Ratio (parts) NPCA/ECA | Adhesive Properties (iron/iron) | | |
|---|---|---|---|
| | Tensile Shear Strength (kgf/cm$^2$) | Hot Tensile Shear Strength (kgf/cm$^2$) | Whitening |
| 0/100 (Comparative example) | 74 | 5 | slightly whitened |
| 20/80 | 80 | 6 | slightly whitened |
| 40/60 | 82 | 8 | not whitened |
| 60/40 | 116 | 28 | not whitened |
| 80/20 | 125 | 45 | not whitened |
| 100/0 | 130 | 45 | not whitened |

COMPARATIVE EXAMPLE

The adhesive properties of neopentyl α-cyanoacrylate were compared with those of n-amyl α-cyanoacrylate (n-AmCA) and iso-amyl α-cyanoacrylate (i-AmCA). The results are as set forth in Table 4.

TABLE 4

| Cyanoacrylate | Chemical Structure | Adhesive Properties (iron/iron) | |
|---|---|---|---|
| | | Tensile Shear Strength (kgf/cm$^2$) | Hot Tensile Shear Strength (kgf/cm$^2$) |
| NPCA | $CH_2=C(CN)(CO_2CH_2C(CH_3)_3)$ | 130 | 45 |
| n-AmCA | $CH_2=C(CN)(CO_2C_5H_{11})$ | 23 | 0 |
| i-AmCA | $CH_2=C(CN)(CO_2CH_2CH_2CH(CH_3)_2)$ | 68 | 0 |

Testing Method

Tensile Shear Strength

Measured at 25° C. after aging 24 hours at 43°±1° C., 60±2% RH, according to JIS K6861.

Hot Tensile Shear Strength

Measureds at 150° C.×1 hr after agint 24 hours at 43°±1° C., 60±2% RH, according to JIS K6861.

Whitening

A schale which had been made clean was placed on black paper, and each adhesive was dropped one drop into the schale. After standing 24 hours at 43° C., 60% RH, the presence or the state of whitening was checked.

What is claimed is:

1. An adhesive composition comprising neopentyl α-cyanoacrylate having the formula

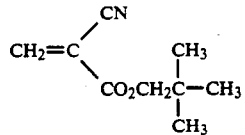

and a second α-cyanoacrylate.

2. An adhesive composition as set forth in claim 1 wherein said second α-cyanoacrylate is a liquid compound at room temperature.

3. An adhesive composition as set forth in claim 1 wherein said neopentyl α-cyanoacrylate is present in a concentration of 5 to 85 wt %, based on the total weight of the α-cyanoacrylate components.

4. An adhesive composition as set forth in claim 3 wherein the concentration of neopentyl α-cyanoacrylate is 60 to 85 wt %, based on the total weight of the α-cyanoacrylate components.

5. An adhesive composition as set forth in claim 1 wherein said second α-cyanoacrylate is selected from the group consisting of methyl α-cyanoacrylate, ethyl α-cyanoacrylate, isopropyl α-cyanoacrylate, 2-methoxyethyl α-cyanoacrylate, 2-ethoxyethyl α-cyanoacrylate, allyl α-cyanoacrylate and propargyl α-cyanoacrylate.

6. An adhesive composition of claim 2 further comprising a stabilizer therefor.

7. An adhesive composition as set forth in claim 6 wherein said stabilizer is selected from the group consisting of sulfurous acid, sulfone compounds, organic sulfonic acids, mercaptans, trifluoroacetic acid, fluoroboric acid, quinones, catechol, pyrogallol and 2,6-di-t-butylphenol.

* * * * *